United States Patent [19]

Bauer et al.

[11] 4,187,222
[45] Feb. 5, 1980

[54] PROCESS FOR THE PREPARATION OF CYCLOPENTADECANOLIDE

[75] Inventors: Kurt Bauer; Alfred Körber, both of Holzminden, Fed. Rep. of Germany

[73] Assignee: Bayer Aktiengesellschaft, Leverkusen, Fed. Rep. of Germany

[21] Appl. No.: 921,158

[22] Filed: Jun. 30, 1978

[30] Foreign Application Priority Data

Jul. 13, 1977 [DE] Fed. Rep. of Germany ....... 2731543

[51] Int. Cl.² ............................................ C07D 313/00
[52] U.S. Cl. ...................................... 260/343; 562/579
[58] Field of Search ......................................... 260/343

[56] References Cited

U.S. PATENT DOCUMENTS

| | | | |
|---|---|---|---|
| 2,092,031 | 9/1937 | Spanagel | 260/343 |
| 3,890,353 | 6/1975 | Becker | 260/343 |
| 4,056,541 | 11/1977 | Hoffman | 260/343 |

FOREIGN PATENT DOCUMENTS 521274 10/1974 U.S.S.R. .................................. 260/343

OTHER PUBLICATIONS

Fiesen et al., Reagents for Organic Synthesis, pp. 248 and 327, John Wiley & Sons, New York.
March, Advanced Organic Chem., McGraw—Hill Book Co. pp. 309 and 310.

Primary Examiner—Alan L. Rotman
Assistant Examiner—Jane T. Fan
Attorney, Agent, or Firm—Sprung, Felfe, Horn, Lynch & Kramer

[57] ABSTRACT

Process for the preparation of cyclopentadecanolide comprising the steps of converting 13-oxa-bicyclo [10.4.0]-hexadecene-[1(12)] to a lactone of the formula

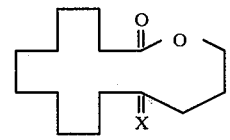

wherein
X is an oxygen atom, =NOH or =N—NH₂,
reducing said lactone to give 15-hydroxy-pentadecanecarboxylic acid and cyclising said acid to give cyclopentadecanolide.

2 Claims, No Drawings

PROCESS FOR THE PREPARATION OF CYCLOPENTADECANOLIDE

The invention relates to a new process for the preparation of cyclopentadecanolide.

Cyclopentadecanolide is a natural musk scent. Various processes for its preparation are known, but these exhibit a number of disadvantages, especially that they only give low yields and that the starting materials are not readily accessible.

Only two processes are of commercial interest. In the process described in U.S. Pat. No. 3,890,353 13-oxa-bicyclo[10.4.0]-hexadecene-[1(12)] which in accordance with U.S. Pat. No. 3,856,815 is readily accessible from cyclododecanone, is converted by means of hydrogen peroxide or an alkyl hydroperoxide into a peroxide, the latter is split, either thermally or by irradiation with UV light, into a mixture of cyclopentadecanolide and cyclopentadecenolide, and the mixture is hydrogenated. The process has the disadvantage that working with peroxides requires special precautionary measures and that the yield of cyclopentadecanolide is at most only 57.9%, relative to 13-oxabicyclo[10.4.0]-hexadecene-[1(12)].

In the second process, 15-hydroxy-pentadecanoic acid is cyclised by vacuum distillation of its polyester (J. Am. Chem. Soc. 58, 654 (1936)). This process has the disadvantage that the starting materials for the preparation of 15-hydroxy-pentadecanoic acid, such as 9,10,16-trihydroxyhexadecanecarboxylic acid (J. Chem. Soc. 1963, 3,505), erucyl alcohol (J. Chem. Soc. 1962, 2,348), or undec-10-enoic acid [Tetrahedron 19, 905 (1963); Japanese Patent Application 68/04,262 (ref. C.A. 70 (1969) 19927z)] are too expensive for a commercial process or are not available in sufficient amount.

U.S.S.R. Patent No. 521 274 (ref. C.A. 86 (1977) Vol. 1, 5536z) describes a process in which 13-oxa-bicyclo[10.4.0]-hexadecene-[1(12)] is converted by means of butyl nitrite/NaHSO$_3$ into 12-ketocyclopentadecanolide and latter is reduced to cyclopentadecanolide by a Clemmensen reaction. However, in this process the yield of cyclopentadecanolide is only 36%, as is apparent from the Examples. Furthermore, the reaction time of 90 hours employed for the Clemmensen reduction is industrially unacceptable.

It is therefore the object of the invention to develop a process which, starting from the readily accessible 13-oxa-bicyclo[10.4.0]-hexadecene-[1(12)], gives cyclopentadecanolide of high purity in good yields and in such a way as to avoid expensive process steps.

According to the invention, this object is achieved if 13-oxa-bicyclo[10.4.0]-hexadecene-[1(12)] is converted, in a manner which is in itself known, into a lactone of the general formula

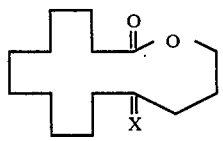

(I)

in which

X denotes an oxygen atom or the group =NOH or =N-NH$_2$, the lactone of the general formula (I) is reduced, with opening of the lactone ring, to give 15-hydroxy-pentadecanecarboxylic acid, and the latter is cyclised in a manner which is in itself known to give cyclopentadecanolide.

Surprisingly, substantially better yields are obtained in the process according to the invention, though this entails an opening of the macrocyclic structure, than in the known processes which also start from 13-oxa-bicyclo[10.4.0]-hexadecene-[1(12)] and in which the macrocyclic structure remains preserved in all the reaction steps. Using the process according to the invention, cyclopentadecanolide of high purity is obtained, by means of process steps which can industrially be carried out effortlessly, in yields of 75 to 85% of theory, based on 13-oxa-bicyclo[10.4.0]-hexadecene-[1(12)].

The conversion of 13-oxa-bicyclo[10.4.0]-hexadecene-[1(12)] into a lactone of the formula (I), in which X represents an oxygen atom, can be carried out as described in DT-OS (German Published Specification) 2,410,859, by ozonolysis of the double bond, or according to J. Org. Chem. 37, 581 (1972), by using an excess of a per-acid.

To convert the 13-oxa-bicyclo[10.4.0]-hexadecene-[1(12)] into a lactone of the formula (I), in which X represents the group =NOH, it has proved advantageous to react 13-oxa-bicyclo[10.4.0]-hexadecene-[1(12)], in accordance with J.C.S. Chem. Comm. 1972, 1078, with nitrosyl chloride or with nitrogen compounds which form nitrosyl ions under the reaction conditions, such as alkyl nitrites or alkali metal nitrites.

The resulting 12-oximinocyclopentadecanolide can subsequently be hydrolysed in a manner which is in itself known, for example by means of sodium bisulphite, to give 12-ketocyclopentadecanolide, that is to say a compound of the formula (I), in which X represents an oxygen atom, or can be converted by means of hydrazine hydrate into the corresponding hydrazone, that is to say a compound of the formula (I), in which X represents the =NNH$_2$ group. The hydrazone can be reduced by the Wolff-Kishner method, using sodium or a sodium alcoholate, the ketone by the Huang-Minlon method with hydrazine in the presence of sodium or potassium hydroxide, with simultaneous scission of the lactone ring, to give 15-hydroxypentadecanoic acid.

However, in a particularly preferred embodiment of the process according to the invention, the 12-oximinocyclopentadecanolide is reduced directly, that is to say without saponifying it to the ketone, with an excess of hydrazine hydrate in the presence of an alkali metal hydroxide, with scission of the lactone ring, to give 15-hydroxypentadecanoic acid. The reductive scission is effected by warming the mixture of oxime, hydrazine and alkali metal hydroxide, in a relatively high-boiling organic solvent, such as ethylene glycol or diethylene glycol, to temperatures of 150° to 200° C.

The molar ratio of hydrazine to 12-oximinocyclopentadecanolide should be between 1.5:1 and 3:1. Hydrazine is preferably employed in the form of 80% strength hydrazine hydrate. Sodium hydroxide or potassium hydroxide are preferably used as the alkali metal hydroxide. The molar ratio of alkali metal hydroxide to 12-oximinocyclopentadecanolide is advantageously from 3:1 to 5:1.

In principle, it is possible to reduce not only the oxime and the hydrazone, but also other azomethine derivatives of 12-ketocyclopentadecanolide, for example the semicarbazone or substituted phenylhydrazones, to 15-hydroxypentadecanoic acid by the Wolff-Kishner or Huang-Minlon method. However, these derivatives offer no advantages over the oxime or hydrazone and instead merely require an additional process step.

The cyclisation of the 15-hydroxypentadecanoic acid can be carried out in accordance with the customary processes, known from the literature, for the preparation of lactones from hydroxycarboxylic acids. A particularly advantageous method has proved to be the abovementioned method of Spanagel and Carothers (J. Am. Chem. Soc. 58, 654 (1936)), in which a linear polyester is first prepared from 15-hydroxypentadecanoic acid and is then depolymerised in the presence of a depolymerisation catalyst, such as magnesium chloride, magnesium oxide, lead dioxide and the like.

Since virtually all intermediate products, and the end product, are obtained in a crystalline form in the process according to the invention, purification is feasible at any stage. In this way, the end product is obtained in high purity and a special purification can be dispensed with.

EXAMPLE 1

A mixture of 221 g (1.85 mols) of isoamyl nitrite, 378 g (1.7 mols) of 13-oxa-bicyclo[10.4.0]-hexadecene-[1(12)], 850 ml of ethanol and 850 ml of water was cooled to −5° C. and 129 ml of 10% strength hydrochloric acid were added dropwise in the course of 75 minutes. The reaction mixture was stirred for 2 hours at 0° to +5° C. and 1,000 ml of water were then added. The crystalline product which precipitated was separated off, washed until neutral, and dried.

Yield: 448.3 g (=97% of theory) of 12-oximinocyclopentadecanolide.

EXAMPLE 2

A mixture of 379.5 g (5.5 mols) of sodium nitrite, 1,110 g (5 mols) of 13-oxa-bicyclo[10.4.0]-hexadecene-[1(12)], 2,520 ml of isopropanol and 2,520 ml of water was cooled to between 0° and +5° C. and 420 g of 38% strength hydrochloric acid were added dropwise in the course of 2 hours within this temperature range. 138 g of 38% strength hydrochloric acid were then added in the course of 20 minutes with particularly intensive cooling. The reaction mixture was stirred for 2 hours at 0° to +5° C. and ice water was then added in the course of 2.5 hours. The crystalline product which precipitated was separated off, washed until neutral, and dried.

Yield: 1,299 g (=95.7% of theory) of 12-oximinocyclopentadecanolide.

EXAMPLE 3

1,000 ml of diethylene glycol were initially introduced into a 4 l three-neck flask provided with an internal thermometer, reflux condenser and stirrer. 280 g (5 mols) of potassium hydroxide, 269 g (1 mol) of 12-oximinocyclopentadecanolide and 187.5 g of 80% strength hydrazine hydrate were then added successively, whilst cooling. The apparatus was then flushed with nitrogen and the reaction mixture was heated for 2 hours to the reflux temperature. The excess hydrazine hydrate was then distilled off as a mixture with water, whilst raising the sump temperature to 185°–195° C. This temperature was maintained until the evolution of nitrogen had ceased (about 9 hours). One liter of ice water was added to the reaction mixture, which was then acidified to a pH value of 2 with hydrochloric acid. The reaction product which precipitated was extracted with warm ethyl acetate. On cooling the warm ethyl acetate solution, the product crystallised out again. It is separated off and dried.

Yield: 239 g (=92.6% of theory) of 15-hydroxypentadecanoic acid; (melting point: 84° C.).

On using 5 mols of lithium hydroxide, sodium hydroxide or sodium ethylate instead of 5 mols of potassium hydroxide, the yields of 15-hydroxypentadecanoic acid were 87 to 91.6% of theory.

EXAMPLE 4

403 g (1.5 mols) of 12-oximinocyclopentadecanolide (prepared according to Example 1), in a mixture of 2 l of ethanol and 2 l of 40% strength sodium bisulphite solution, were heated for 2.5 hours to the reflux temperature. The reaction mixture was then mixed with 3 l of water and extracted with ether. The organic phase was separated off, washed until neutral and dried. The solvent was then distilled off and the residue was distilled in vacuo (boiling point: 150°–153° C./1.3 mm Hg).

Yield: 332 g (=87% of theory) of 12-keto-cyclopentadecanolide.

EXAMPLE 5

50 g of 12-keto-cyclopentadecanolide (prepared as described in Example 4) were reacted with 36.6 of 80% strength hydrazine hydrate and 54.7 g of potassium hydroxide in 150 ml of diethylene glycol under the reaction conditions described in Example 3.

Yield: 48 g (94.4% of theory) of 15-hydroxypentadecanoic acid.

EXAMPLE 6

385 g (1.49 mols) of 15-hydroxypentadecanoic acid were heated in a distillation apparatus for 3 hours to 160° C. A waterpump vacuum was then applied in order to remove the residual water. The residue was mixed with 23 g of magnesium chloride and dropped, whilst stirring, under a vacuum of 0.5 mm Hg into a distillation apparatus pre-heated to 280° C. 330 g (92.3% of theory, based on 15-hydroxypentadecanoic acid employed) of cyclopentadecanolide passed over at 140° C./0.5 mm Hg.

What is claimed is:

1. In a process for the preparation of cyclopentadecanolide from 13-oxa-bicyclo[10.4.0]-hexadecane-[1(12)] by oxidizing the starting material to the 12-keto-cyclopentadecanolide and converting the keto-lactone to cyclopentadecanolide, the improvement which comprises converting the 12-keto-cyclopentadecanolide or its oxime to the cyclopentadecanolide by reduction with hydrazine in the presence of an alkaline catalyst to form the linear hydroxyacid and thereafter closing the ring.

2. A process according to claim 1, wherein the oxidation of the 13-oxa-bicyclo[10.4.0]-hexadecane-[1(12)] is effected with nitrosyl chloride or a nitrogen compound which forms nitrosyl ions under the reaction conditions to form the oximino-lactone, the oximino-lactone is converted by means of hydrazine hydrate in the presence of alkali metal hydroxide to form 15-hydroxypentadecanoic acid, and the acid is ring closed by polymerizing it to a linear polyester followed by depolymerization and ring closure in the presence of a depolymerization catalyst.

* * * * *

UNITED STATES PATENT AND TRADEMARK OFFICE
CERTIFICATE OF CORRECTION

PATENT NO. : 4,187,222
DATED : February 5, 1980
INVENTOR(S) : Kurt Bauer et al

It is certified that error appears in the above-identified patent and that said Letters Patent are hereby corrected as shown below:

Item [73] "Bayer Atkiengesellschaft, Leverkusen, Fed. Rep. of Germany" should be --Haarmann & Reimer GmbH., Holzminden, Fed. Rep. of Germany--.

Signed and Sealed this

Twenty-third Day of December 1980

[SEAL]

*Attest:*

SIDNEY A. DIAMOND

*Attesting Officer*     *Commissioner of Patents and Trademarks*